United States Patent [19]
Esformes et al.

[11] 4,332,037
[45] Jun. 1, 1982

[54] ARTIFICIAL JOINT

[75] Inventors: Ira Esformes, New York, N.Y.; Frederick J. Kummer, Hackensack, N.J.

[73] Assignee: Hospital for Joint Disease Orthopaedic Institute, New York, N.Y.

[21] Appl. No.: 216,114

[22] Filed: Dec. 15, 1980

[51] Int. Cl.³ .............................................. A61F 1/24
[52] U.S. Cl. .................................... 3/1.91; 128/92 C
[58] Field of Search ................................ 3/1.9–1.913; 128/92 C, 92 CA

[56] References Cited

U.S. PATENT DOCUMENTS

| 2,696,817 | 12/1954 | Prevo | 3/1.91 X |
| 3,805,302 | 4/1974 | Mathys | 3/1.91 |
| 3,813,700 | 6/1974 | Tavernetti et al. | 3/1.91 |
| 3,899,796 | 8/1975 | Bahler et al. | 3/1.91 |
| 3,990,117 | 11/1976 | Pritchard et al. | 3/1.91 |
| 4,024,588 | 5/1977 | Janssen et al. | 3/1.91 |
| 4,079,469 | 3/1978 | Wadsworth | 3/1.91 |
| 4,224,695 | 9/1980 | Grundei et al. | 3/1.91 |

FOREIGN PATENT DOCUMENTS

| 541963 | 11/1973 | Switzerland | 3/1.91 |
| 591845 | 9/1977 | Switzerland | 3/1.911 |

*Primary Examiner*—Ronald L. Frinks
*Attorney, Agent, or Firm*—Jordan and Hamburg

[57] ABSTRACT

An artificial joint for implantation into a living body comprising two members held together by magnetic forces of attraction with the magnetic lines of force running substantially along the direction of the pivotal axis and transversely across the primary direction of movement of the two members.

17 Claims, 11 Drawing Figures

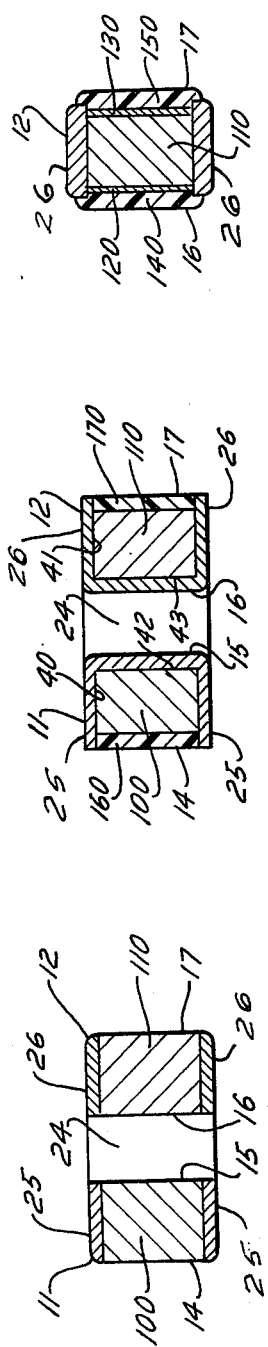

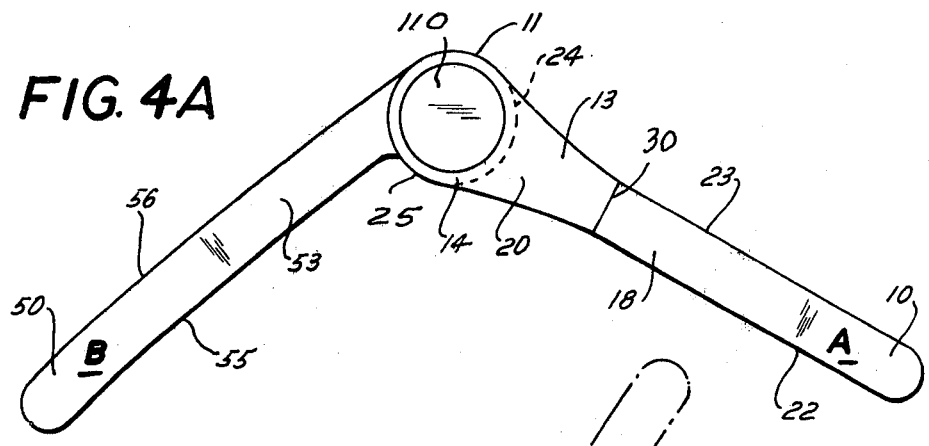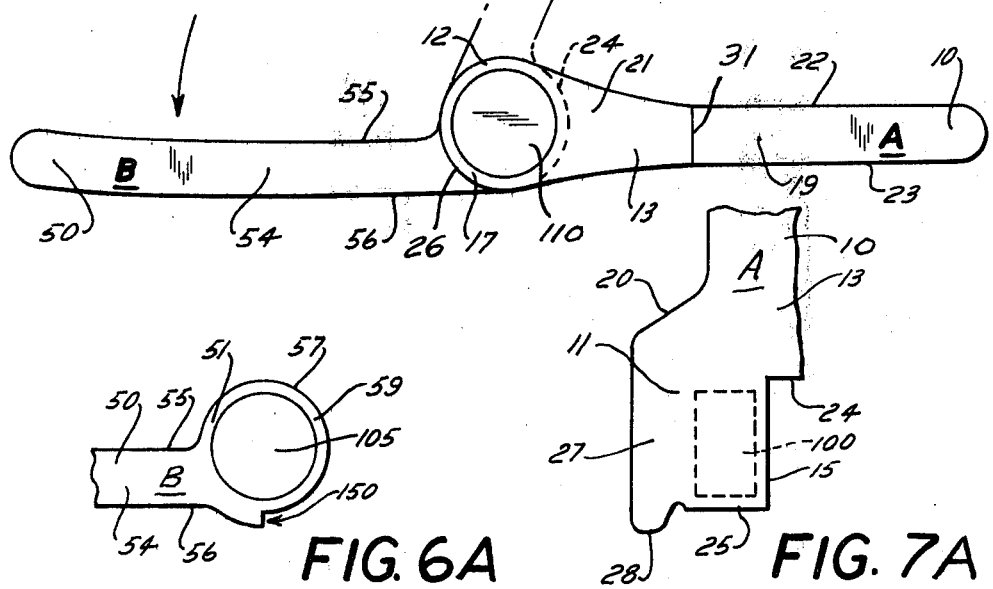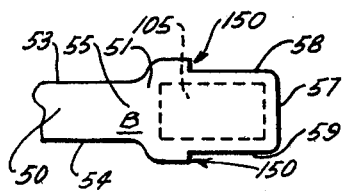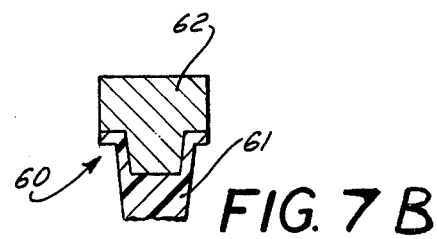

ARTIFICIAL JOINT

BACKGROUND OF THE INVENTION AND PRIOR ART STATEMENT

The present invention is directed to an artificial joint for implantation into the living body.

Different types of artificial or prosthetic joints have been known for some time. The stability of a total joint prosthesis is a compromise between biomechanics of design and integrity of existing biological structures. A constrained prosthetic device, such as one disclosed at M. Post et al, *Clin. Orth. and Rel. Res.* 144 (1979) p. 135, creates significant forces and pressure within the bone-cement-prosthesis interface with the danger of subsequent loosening or failure of the device itself. A unconstrained prosthetic device, as disclosed at S.A.V. Swanson, *J. Biomed. Eng.* Vol. 1, p. 253 (1976), has the propensity for dislocation.

Artifical joints dependent on magnetic force intersaction have been attempted before. For example, U.S. Pat. No. 4,024,588 of Janssen et al, issued May 24, 1977, discloses a prosthetic joint of head and socket construction with at least one implanted magnet for fostering mutual rotational and translational movement of these portions about their point of pivoting (column 2, lines 22-26). The magnetic force generated may be either of attraction or repulsion. The patentees have also disclosed their work in this area in *Z. Orthop.* 133 (1975) pp. 400-401.

The prosthetic joint disclosed in U.S. Pat. No. 4,024,588 has several attendant difficulties in that the magnetic field lines of force pass directly along the axes or direction of motion of the head and socket members. The point of contact between the head and socket members is subjected to increased force which can lead to greater wear generated by the magnetic lines of force. If magnetic force of repulsion is employed, then the joint members can be subject to floating and ultimate dislocation. If magnetic force of attraction between members is utilized, then the artificial joint could be subject to inelastic transmission of shocks along the skeletal structure with propensity for further skeletal injury or joint dislocation too. This, in fact, is a problem even recognized in U.S. Pat. No. 4,024,588 at column 2, lines 29-40.

Accordingly, it is an object of the present invention to provide an artificial joint for insertion into the living body with a minimum of external features or connective arrangements.

It is also an object of the present invention to provide an artificial joint based on magnetic attraction wherein magnetic attraction between joint members acts to maintain the stability and integrity of the artificial joint without interfering with the movement of the joint members.

It is still a further object of the present invention to provide an artificial joint based on magnetic attraction between joint members wherein freedom of movement of joint members closely simulates the natural joint being replaced.

Other objectives of the present invention will be readily apparent from the disclosure herein.

SUMMARY OF THE INVENTION

The present invention concerns an artificial joint for implantation into a living body which comprises two members or components held together by magnetic forces of attraction. Magnets are situated in either one or the other or both of these components with the magnetic lines of force running transversely across the primary direction of movement of the two components (perpendicular to the primary direction of movement for the components). The artificial joint is securely held in place by magnetic forces of attraction which do not interfere with the freedom of movement of the artificial joint components. Thus requirements of pins, hinges, and other outside connective means are effectively eliminated from artificial joints of the present invention. Additionally, should the need arise, these artificial joints could be separated during surgery with a minimal amount of effort.

An artificial joint of the present invention may effectively replace any of the natural joints in a living body. In a preferred embodiment, the artificial joint comprises two components which are snugly mated, as illustrated in the figures. Such an artificial joint may be implanted in any of a number of locations in the living body, but is especially suitable for replacement of elbow and digital joints. The present invention will now be described in more detail with reference to the drawings.

BRIEF DESCRIPTION OF THE DRAWINGS

FIG. 1 is an exploded right side view of an artificial joint structure in accordance with the present invention comprising two components, A and B;

FIG. 2 is an exploded top view of the artificial joint illustrated in FIG. 1;

FIG. 3 is a sectional view of component A of the artificial joint of the present invention taken along lines III—III of FIG. 2;

FIGS. 4(A) and 4(B) are side views of two possible orientations of the artificial joint of the present invention when the components are engaged;

FIGS. 5(A) and 5(B) are sectional views of alternative implantations of magnets within the artificial joint of the present invention;

FIGS. 6(A) and 6(B) are partial side and top views of modifications to component B of the artificial joint of the present invention;

FIG. 7(A) is a partial top view of a further modification to component A of the artificial joint; and FIG. 7(B) is a sectional view of an element for articulating with the modification to component A.

DETAILED DESCRIPTION OF PREFERRED EMBODIMENTS

The following description is intended as an illustration of an embodiment of the present invention and is not intended to limit the scope of the present invention or of any other embodiments thereof.

Referring to the figures, notably FIGS. 1 and 2, the illustrated embodiment of the present invention comprises two components A and B. The first component A comprises a stem 10, which branches out at one end into two bifurcated portions 11 and 12. More specifically, the stem branches into an expanded base portion 12 at corners 30 and 31, which in turn, branches into the two bifurcated base portions 11 and 12 with respective surfaces 25 and 26 as illustrated. The sides of the two bifurcated portions 14, 15, 16 and 17 are substantially parallel to the sides 18 and 19 of the stem, with the sides 20, 21 of the expanded base portion 13 extending obliquely between the sides of the bifurcated portions and of the stem as illustrated. Additionally, the top surface 22 of the stem 10 and its bottom surface 23 (hidden from view in FIG. 2) together with the sides 18, 19 of the stem 10, form a stem of approximately rectangular cross-sectional area in this illustrated embodiment. However, the stem of component A, or of component B too, may be shaped with any convenient cross-sectional area, such as circular, triangular diamond-shaped, pentagonal, hexagonal, etc. Additionally, the sides and edges of the stems may be crenulated, serrated or textured to aid in fixation of the stem to bone tissue with acrylic bone cement.

As noted supra, the sides 20, 21 of the expanded base portion 13 of the stem extend obliquely between the sides of the stem (beginning at corners 30 and 31) and the bifurcated base portions 11 and 12 to give an approximately triangular appearance of the expanded base portion 13 as illustrated in FIG. 2. Additionally, the top surface 22 of the stem 10 runs roughly parallel to the bottom surface 23 through the balance of the stem 10. There is a slight curvature to the top surface 22 of the stem 10 of component A. This is so the axis of the stem parallels the axis of the bone into which the stem is inserted, such as the humeral bone. This is best illustrated in the side view of FIG. 1 where it is seen that both top and bottom surfaces 22 and 23 of the stem gradually form the bifurcated base portion 12, together with the side 17 thereof. The same configuration is true for bifurcated base portion 11, hidden in this particular view. The bifurcated base portions 11 and 12 themselves may take any convenient shape or configuration. In the illustrated embodiment, the bifurcated portions are approximately cylindrical in shape, best seen in the top view of FIG. 2. Additionally, there is a recessed internal concavity portion 24 in the expanded base portion 13 of the stem 10, between the two bifurcated portions, indicated by the dotted line in the side view of FIG. 1 and best seen in the sectional view of FIG. 3. The purpose of this recessed portion is to snugly receive component B when the two components A and B are engaged, as will be explained in greater detail infra.

The second component B comprises a stem 50 which at one end is formed into an enlarged head portion 51 with sides 58 and 59, and surface 57 as illustrated. As noted supra, the stem 50 may take any convenient shape or configuration. In the presently illustrated embodiment, the sides 53 and 54 and the top and bottom surfaces 55 and 56 form a stem of approximately rectangular cross-section. Additionally, the top and bottom surfaces 55 and 56 of the stem are slightly curved for affixation to appropriate bone tissue, though these surfaces may be completely straight or take any convenient form.

The head 51 of the stem 50 of component B is approximately cylindrically shaped as are the bifurcated base portions 11 and 12 of component A. When the two components A and B are engaged, the head portion 51 of component B will snugly mate with the internal concavity 24 between the bifurcated portions 11 and 12 of component A forming a point of engagement of the two components having a pivotal axis about which the components pivot in a primary direction of movement. FIGS. 4(A) and 4(B) illustrate two such possible engaging positions of components A and B. In FIG. 4(A) components A and B are engaged in an inverted position at an angle whereas in FIG. 4(B) components A and B are engaged at fully extended positions. Generally, the radius of curvature of the recessed area 24 of component A is slightly larger than the radius of curvature of the head portion 51 of component B, and the width of cylindrical base portion 51 of component B is slightly smaller than the distance between sides 15 and 16 of the bifurcated cylindrical portions 11 and 12 of component A to allow for complete freedom of movement when the components are engaged. The degree of motion between components of this joint will range from 0° when the components are fully extended to about 135° in full flexion (see dotted lines, for example, in FIG. 4(B)). Additionally, the fact that the width of the head 51 of component B is slightly smaller than the distance between the two bifurcated base portions of component A allows for A-P laxity (anterior-posterior laxity) between components of the artificial joint. Thus, the artificial joint of the present invention may successfully simulate movement conditions of natural joints in the body such as elbow joints, digital joints, and the like.

The components of the artificial joint of the present invention may be constructed of any suitable material for implantation with the living body, such as aluminum, polymethyl methacrylate, silicone rubber, and cobalt-chrome. Preferred material for construction is 316L stainless steel cobalt-chromium-molybdenum (commercially available as Vitallium, Orthochrome and Zimalloy) and titanium (such as Ti-6Al-4V alloy). Aluminum joints of the present invention may be prepared by conventional machining processing while cobalt-chrome joints may constructed by the lost wax process and be precision-cast.

In the illustrated embodiment, the bifurcated base portions 11 and 12 of component A each have magnets 100 and 110 implanted in them respectively, as does the head 51 of component (magnet 105). The magnets 100, 105, and 110 are approximately cylindrical in shape though they may take any convenient form. These magnets are constructed of any permanent magnetic material such as cobalt-samarium ($Co_5Sm$), cobalt-rare earth or high energy product permanent magnets. The preferred magnetic material is $Co_5Sm$.

The magnets are inserted and held in place with the aid of suitable adhesive to effectively encapsulate the magnets and prevent them from chipping or incurring other damage (FIGS. 5(A) and (B) for example). Suitable encapsulating material includes polyethylene, medical grade epoxy, and silicone rubber (medical grade) with especially preferred encapsulating materials being epoxy-based compounds or high molecular weight polyethylene. Additionally, the magnets may be layered with polyethylene inserts prior to encapsulating. FIG. 5(B) illustrates the encapsulation of magnet 110 in bifurcated base portion 12 of component A where the magnet is initially layered with polyethylene inserts 120 and 130 before the outer encapsulating material 140 and 150 is applied to sides 16 and 17 respectively of the bifurcated base portion 12, over the polyethylene inserts 120 and 130 respectively. Recess 24 in component A is preferably coated with high molecular weight polyethylene to prevent undue wear against the surface 57 of head 51 of component B. Therefore all magnets in the artificial joint are preferably shielded from contacting each other, from contacting other components at the point of engagement, and from contacting outside body tissue, so that only emanating magnetic lines of force will have effect on the operation of the artificial joint.

In an alternative embodiment (illustrated in the cross-sectional view of FIG. 5(A)), the magnets 100 and 110 do not extend throughout the width of the respective bifurcated base portions 11 and 12 of component A, but are rather positioned in recessed wells 40 and 41 within these bifurcated sections so that the bases 42 and 43 of these wells terminate at a point near the inner sides 15 and 16 of these bifurcated portions. Therefore, these magnets need only be sealed in place at the outer sides or extremities 14 and 17 of bifurcated portions 11 and 12 with outer encapsulating material 160 and 170 respectively. However, the magnetic lines of force still penetrate the inner walls 15 and 16 of the bifurcated base portions, as the construction materials of the artificial joint are permeable to magnetic lines of force. Therefore, the net magnetic effect of this particular type of embodiment is identical to all other embodiments of the present invention, and the magnetic forces are not appreciably diminished or hindered in any way.

The various magnets are positioned in the components of the artificial joint to generate a force of attraction between the two components when they are cooperatively engaged. The magnets are arranged in bifurcated base portions 11 and 12 of component A and in head 51 of component B to foster attraction between the two components when they are brought together in a certain fashion (see, for example, FIGS. 4(A) and (B)) and foster repulsion if one or the other components are inverted. Thus the polar arrangement of magnets within this artificial joint helps assure that the two components A and B cannot easily be coupled or engaged in the wrong direction or fashion. Alternatively, magnets may be omitted from one or the other bifurcated base portions of component A or from the head 51 of component B, so long as attractive force will still be generated when the components are engaged in the desired fashion (the magnets may be replaced by a ferromagnetic material which is still responsive to magnetic attraction).

The magnets are positioned in the components of the artificial joint with the magnetic lines of force running transversely across or perpendicular to the primary direction of movement (or direction of pivoting) of the two components A and B when they are cooperatively engaged. As a result, the magnetic restraint caused by the forces of attraction between magnets in the two components acts only against displacement of the component parts of the artificial joint and not against rotation, either flexion or extension, of the component members as they pivot about the point of co-operative engagement. Thus, the artificial joint of the present invention provides increased stability and integrity of the muscular-skeletal structure in the living body, providing repositioning and augmentation of muscles and ligaments in the area of the artificial joint.

The embodiment illustrated in the figures is especially suitable as an artificial elbow or digital joint. In an artificial elbow joint, component A is the humeral component, and is adapted for insertion into a preformed cavity within the humerus. The stem 10 of component A has a length of from about 10 cm to about 12 cm and a cross section from about 2 cm$^2$ to about 1 cm$^2$. The oblique sides 20 and 21 of the expanded base portion 13 are from about 2 cm to about 2.5 cm in length and the radii of each of the distal and proximal bifurcated base portions 11 and 12 respectively is from about 1 cm to about 1.25 cm. The surfaces 25 and 26 of the respective cylindrically-shaped bifurcated base portions 11 and 12 are from about 0.75 cm to about 0.95 cm in width, and the distance between inner sides 15 and 16 is from about 0.85 cm to about 1.05 cm (the approximate width of internal concavity 24). Additionally, internal concavity 24 has an approximate radius of curvature from about 1 cm to about 1.25 cm.

The center of the bifurcated cylindrically-shaped base portions 11 and 12 is offset from the central axis of the stem 10 about 5° to 10° preferably about 7°, from a point on the central axis near the beginning of expanded base portion 13 where sides 20 and 21 meet sides 18 and 19 of the stem 10 (corners 30 and 31). This is so the contours of component A will closely follow the physiological contours of the humeral condyle that component A is replacing. The bifurcated base portions may be preformed along with the stem 10 of component A or may be formed separately and then attached to the stem 10 of component A with suitable adhesive or the like.

Component B is the ulnar component, adapted for insertion into a preformed cavity provided in the ulnar bone. In component B, the stem 50 is from about 6 cm to about 8 cm in length and has a cross-sectional area from about 1 cm$^2$ to about 1.5 cm$^2$. The cylindrically-shaped head 51 of component B has a radius from about 1 cm to about 1.25 cm and a width from about 0.75 cm to about 0.95 cm or slightly smaller than the width of internal concavity 24 in component A to allow for natural A-P laxity. Additionally, the radius of head 51 is slightly smaller than the radius of curvature of internal concavity 24 to allow for greater freedom of movement of the ulnar component.

The magnets utilized in an artificial elbow joint of this embodiment are cobalt-samarium of approximate power 8000 GAUSS. This elbow joint allows for full rotation of articulated components from 1°–135° (±5° due to internal bearing gap). However, abutments or stops 150 may be placed along head 51 of component B if less rotation is desired. Two such embodiments are illustrated in FIGS. 6(A) and (B) respectively. Additionally, a high molecular weight polyethylene layer may be glued or snap-fitted to the surface of internal concavity 24 in component A to prevent undue wear-and-tear between joint components. The disarticulation force of this elbow joint at full extension (0°) is approximately 3 kg, sufficient to support the unloaded forearm.

In a further modification of this elbow joint (see FIG. 7(A)), the distal bifurcated portion 11 of component A is provided with a convex protusion 27 extending outwardly and in a forward direction thereof. This outward and forward protusion 27 is adapted to articulate with with the radius bone in the body at surface 28, preferably by contacting a polyethylene radial insert 60 in the radial bone. This polyethylene insert, illustrated in the sectional view of FIG. 7(B), comprises a metal stem 61 with a polyethylene backed head 62 and is inserted into the radial bone by any of the conventional bone prosthetic insertion techniques. A single solid polyethylene piece can be substituted for the illustrated insert. This particular embodiment greatly provides increased stability at the elbow joint, notably at the point of humeral-radial articulation.

As noted previously, the illustrated embodiment is also suitable for replacement of digital joints. In these circumstances, the stem 10 of component A is approximately 2 cm to 3 cm in length with a cross sectional area from about 1 cm to about 0.25 cm. Oblique sides 20 and 21 of expanded base portion 13 are from about 0.75 cm to about 1 cm in length and the radii of the cylindrically-shaped bifurcated base portions 11 and 12 are from about 0.4 cm to about 0.5 cm, with the width of surfaces 25 and 26 of these bifurcated base portions from about 0.25 cm to about 0.35 cm. The distance between inner sides 15 and 16 of the bifurcated base portions 11 and 12 is from about 0.3 cm to about 0.5 cm and the approximate radius of curvature of internal concavity 24 is from about 0.4 cm to about 0.5 cm. Component B has a stem 50 from about 1 cm to about 1.5 cm in length with a cross-sectional area from about 0.75 cm$^2$ to about 0.25 cm$^2$. Cylindrically-shaped head 51 in component B has a radius of about 0.4 cm to about 0.5 cm, and a width from about 0.25 cm to about 0.4 cm, slightly smaller than the width of the internal concavity 24 in component A.

While the preferred specific embodiments have been described above and illustrated in the drawings, the shape and material of the components of the artificial joints as well as the shape and material of the type of magnets may vary to simulate the respective joints in the living body as closely as possible. Accordingly, the foregoing description of preferred embodiments is not intended to limit invention scope.

What is claimed is:

1. An artificial joint for implantation into a living body comprising:
    (A) a first component, and
    (B) a second component which cooperatively engages said first component, forming a point of engagement having a pivotal axis about which said two components pivot in a primary direction of movement, and (C) a magnet positioned in at least one of said two components with the magnetic lines of force flowing substantially along said pivotal axis and transversely across said primary direction in which said two components pivot
    so that said two components are attracted to one another when cooperatively engaged.

2. An artificial joint of claim 1 wherein a magnet is positioned in both said components.

3. An artificial joint of claim 1 wherein said first component is recessed to receive said second component in cooperative engagement.

4. An artificial joint of claim 3 wherein at least one magnet is positioned adjacent the recessed area in said first component.

5. An artificial joint of claim 4 wherein a magnet is positioned in either side of said recessed area.

6. An artificial joint of claim 5 wherein a magnet is positioned in said second component.

7. An artificial joint of claim 3 which is an elbow joint.

8. An artificial joint of claim 3 which is a digital joint.

9. An artificial joint of claims 7 or 8 wherein (A) said first component comprises a stem that is recessed at one end, and
    (B) said second component comprises a stem with an enlarged area at one end of said stem, for cooperatively engaging said first component in the recessed area.

10. An artificial joint of claim 9 wherein the stem of said first component is enlarged around either side of the recessed area for retaining the enlarged area of said second component
    so that the recessed area is slightly larger than the enlarged area of said second component.

11. An artificial joint of claim 10 wherein said first component is to be affixed to the humeral bone in a living body and said second component is to be affixed to the ulnar bone in a human body.

12. An artificial joint of claim 11 wherein magnets are positioned in both enlarged areas of the stem of said first component.

13. An artificial joint of claim 11 wherein a magnet is positioned in the enlarged area of the stem of said second component.

14. An artificial joint of claim 11 wherein magnets are positioned in all enlarged portions of the stems of both said first and second components.

15. An artificial joint of claim 11 wherein the enlarged distal area of said first component additionally comprises a protusion for contacting the radius bone of a living body to provide additional stability when the components of the artificial joint are cooperatively engaged.

16. An artificial joint of claim 11 wherein the enlarged areas of the stems of both said first and second components are substantially cylindrical in shape with the recessed area of said first component substantially curved to receive the enlarged area of the stem of the second component.

17. An artificial joint of claim 15 wherein the distal protrusion contacts an artificial insert adapted to be inserted into the radius bone.

* * * * *

UNITED STATES PATENT AND TRADEMARK OFFICE
CERTIFICATE OF CORRECTION

PATENT NO. : 4,332,037
DATED : June 1, 1982
INVENTOR(S) : Ira Esformes et al

It is certified that error appears in the above-identified patent and that said Letters Patent are hereby corrected as shown below:

column 2, line 60, change "12" to --13--.

Signed and Sealed this

Seventeenth Day of August 1982

[SEAL]

Attest:

GERALD J. MOSSINGHOFF

Attesting Officer     Commissioner of Patents and Trademarks